United States Patent
Keranen et al.

(10) Patent No.: US 9,423,245 B2
(45) Date of Patent: Aug. 23, 2016

(54) ARRANGEMENT FOR OPTICAL MEASUREMENTS AND RELATED METHOD

(71) Applicants: Heimo Keranen, Oulu (FI); Petri Lehtonen, Oulu (FI)

(72) Inventors: Heimo Keranen, Oulu (FI); Petri Lehtonen, Oulu (FI)

(73) Assignee: HELMEE IMAGING OY, Tampere (FI)

( * ) Notice: Subject to any disclaimer, the term of this patent is extended or adjusted under 35 U.S.C. 154(b) by 133 days.

(21) Appl. No.: 14/370,547

(22) PCT Filed: Dec. 20, 2012

(86) PCT No.: PCT/EP2012/076345
§ 371 (c)(1),
(2) Date: Jul. 3, 2014

(87) PCT Pub. No.: WO2013/102572
PCT Pub. Date: Jul. 11, 2013

(65) Prior Publication Data
US 2014/0376003 A1    Dec. 25, 2014

(30) Foreign Application Priority Data
Jan. 5, 2012    (FI) ...................................... 20125014

(51) Int. Cl.
*G01B 11/24* (2006.01)
*G01N 21/956* (2006.01)
*G01B 11/245* (2006.01)

(52) U.S. Cl.
CPC .............. *G01B 11/24* (2013.01); *G01B 11/245* (2013.01); *G01N 21/956* (2013.01); *G01N 2201/062* (2013.01)

(58) Field of Classification Search
CPC . G01B 11/24; G01N 21/956; G01N 2201/062
USPC .............................. 356/601–625; 348/131, 126
See application file for complete search history.

(56) References Cited

U.S. PATENT DOCUMENTS

| 4,427,880 A | 1/1984 | Kanade et al. |
| 5,060,065 A | 10/1991 | Wasserman |

(Continued)

FOREIGN PATENT DOCUMENTS

WO    2010/090604 A1    8/2010

OTHER PUBLICATIONS

Sanderson A C et al.: "Structured Highlight Inspection of Specular Surfaces", Transactions on Pattern Analysis and Machine Intelligence. IEEE. Piscataway, USA, vol. 10. No. 1. Jan. 1, 1998. pp. 44-55, XP002287715, ISSN: 0162-8828. 001: 10.1109/34.3866 abstract p. 44-p. 54 figures 1. 2. 13-17.

(Continued)

*Primary Examiner* — Sang Nguyen
(74) *Attorney, Agent, or Firm* — Young & Thompson (57) ABSTRACT

An arrangement for optically measuring the surface of an optionally glossy target object, includes: a diffusive, semi-transparent illumination structure defining a hollow surface shape configured to surround the target object at least partially, the surface being further provided with at least two apertures, a number of light sources optically coupled to the diffusive illumination structure for illuminating the target object via the surface of the illumination structure, at least two imaging devices, each configured to image the target object via an aperture, and a control entity configured to instruct the number of light sources to form a sequence of predetermined illumination patterns illuminating the target object, to instruct the at least two imaging devices to obtain an image of the target object relative to each illumination pattern, and to derive, through the utilization of the patterns utilized and images obtained, a predetermined surface-related property of the target object.

21 Claims, 5 Drawing Sheets

(56) References Cited

U.S. PATENT DOCUMENTS

| | | | |
|---|---|---|---|
| 5,245,421 A | 9/1993 | Robertson et al. | |
| 5,365,084 A * | 11/1994 | Cochran | G01N 21/8901 250/226 |
| 5,461,417 A * | 10/1995 | White | G01N 21/8806 348/125 |
| 5,644,140 A * | 7/1997 | Biedermann | G01N 21/8806 250/239 |
| 6,222,630 B1 | 4/2001 | Wasserman | |
| 6,618,123 B2 * | 9/2003 | Uomori | G01S 7/4815 348/131 |
| 6,730,926 B2 * | 5/2004 | Boillot | G01V 8/22 250/559.19 |
| 6,788,411 B1 * | 9/2004 | Lebens | G01N 21/21 356/364 |
| 7,075,565 B1 * | 7/2006 | Raymond | G01N 21/95684 348/126 |
| 7,256,895 B2 * | 8/2007 | Castonguay | G01N 21/474 356/446 |
| 7,349,096 B2 * | 3/2008 | Wadman | G01B 11/303 356/446 |
| 8,032,017 B2 * | 10/2011 | Pastore | G03B 15/06 348/131 |
| 2002/0196338 A1 * | 12/2002 | Tham | G01N 21/8806 348/131 |
| 2005/0156103 A1 * | 7/2005 | May | F21K 9/54 250/228 |
| 2006/0109345 A1 * | 5/2006 | Stenger | G01R 31/309 348/92 |
| 2006/0180775 A1 | 8/2006 | Paradis | |
| 2008/0137088 A1 | 6/2008 | Wagner | |
| 2010/0259746 A1 | 10/2010 | Ohnishi et al. | |
| 2011/0262007 A1 * | 10/2011 | Kojima | G01B 11/2509 382/103 |
| 2012/0044504 A1 * | 2/2012 | Ohnishi | G01B 11/24 356/602 |
| 2012/0086950 A1 * | 4/2012 | Sho | G01B 11/2509 356/601 |

OTHER PUBLICATIONS

FI Search Report, dated Aug. 31, 2012, from corresponding FI application.
International Search Report, dated Apr. 10, 2013, from corresponding PCT application.
Finnish Office Action and Search Report, dated Jan. 22, 2015, from corresponding FI application.

* cited by examiner

ARRANGEMENT FOR OPTICAL MEASUREMENTS AND RELATED METHOD

FIELD OF THE INVENTION

Generally the present invention relates to optics. In particular, however not exclusively, the present invention concerns optical measurements for determining the topography of target objects.

BACKGROUND

Measuring the topography of high-curvature surfaces associated with various objects has in many occasions turned out difficult. Traditional optical methods are limited to flat surfaces. For small and flat surfaces e.g. interferometers can be used, but they are expensive, slow and provide unacceptable accuracy.

Different methods incorporating physical contact with the target objects are also often tedious, provide inferior horizontal resolution and even scratch or otherwise damage the potentially delicate surface under analysis. Such drawbacks are rather comprehensible in the light of point-by-point scanning methods typically applied. Alternative machine vision—based arrangements do not perform too well either, particularly in connection with glossy surfaces.

Shape measurement of high-curvature glossy objects is indeed generally demanding to say the least. Currently e.g. the quality control of glossy objects is made manually using visual inspection in bright illumination. The outcome of such inspection depends highly of the expertise of the particular human inspector in charge and varies also with time and the manufacturing process itself. Using manual inspection only rather vague qualitative results can be obtained; more characterizing, or at least more exact, numerical values representative of the defects or 3d shape remain practically secret. However, many glossy products are considered as high quality or 'high end' products, whereupon even small defects should be preferably identified during or briefly after the manufacture thereof.

One optical method for tracking glossy surfaces is based on the use of a flat digital display (e.g. TFT-monitor) and a camera. The display may be arranged to show fringe patterns and the camera may observe patterns as reflected via the tested surface. Analysis regarding the phase changes of the pattern between original and reflected version may then reveal the slope of the surface with reasonable accuracy and overall execution time, but the applicable maximum curvature of the object stays rather limited, i.e. the object shall be still be relatively flat for obtaining comprehensive analysis results of decent accuracy.

SUMMARY OF THE INVENTION

The objective is to at least alleviate one or more aforesaid problems and to provide an arrangement and related method for measuring the shape of a target object optionally having a glossy surface.

The objective is achieved by different embodiments of an arrangement for optically measuring the surface, such as surface shape and/or surface defects, of an optionally glossy target object, comprising:

a diffusive, semi-transparent illumination structure defining a hollow, preferably curved, surface shape configured to surround the target object at least partially, preferably substantially at least hemispherically, the surface being further provided with at least two, preferably substantially pinhole-like and optionally lens-provided, apertures, a number of light sources optically coupled to the diffusive illumination structure for illuminating the target object via the surface of the illumination structure, at least two imaging devices, each configured to image the target object via an aperture of said at least two apertures, and a control entity configured to instruct the number of light sources to form an image sequence of predetermined illumination patterns on the surface of the illumination structure to illuminate the target object with said patterns projected via the surface, to instruct the at least two imaging devices to obtain an image of the target object relative to each illumination pattern, and to derive, through the utilization of said patterns utilized and images obtained, a predetermined surface-related property of the target object.

In one embodiment, the arrangement, in particular e.g. the control entity thereof, may be configured to apply the image data of multiple images to determine the position and/or orientation of a surface element of the target object through determination of an imaging element, such as a pixel, pair including an imaging element from each of two imaging devices, wherein the surface element is in mirror angle relative to both imaging elements in view of two light-transmitting surface locations of the illumination structure and the associated rays reflected from the surface element.

The arrangement may be thus configured to deduce the actual orientation of the surface element based on the mirror angle found.

Optionally, the arrangement may be further configured to determine the position of the surface element of the target object based on said imaging element pair and calibration information regarding the relationship of different imaging elements between the two imaging devices, said information preferably indicating knowledge about potential light ray intersections between the imaging elements of the imaging devices such as intersection locations.

In another, either supplementary or alternative, embodiment the arrangement is configured to determine for a first imaging element, such as a pixel, of a first imaging device, a matching first light-transmitting surface location of the illumination structure based on image data of multiple images obtained, said first light-transmitting surface location supplying light to the first imaging element via an actual mirroring surface element of the target object, utilizing said first imaging element and the associated first aperture of said illumination structure, a first line defining a plurality of potential surface elements each of which having a certain orientation and being in mirror angle relative to said first surface location and said first imaging element, said plurality of potential surface elements also containing said actual mirroring surface element, a second imaging element, such as a pixel, of a second imaging device, with a matching, second light-transmitting surface location of the illumination structure based on image data of multiple images obtained, wherein the second image element and the associated second aperture of the illumination structure define a second line having an intersection with the first line at one of said plurality of potential surface elements also being in mirror angle relative to said second surface location and said second imaging element, said one of said plurality of potential surface elements being thus indicative of said actual mirroring surface element including the orientation thereof, and the position of the actual mirroring surface element utilizing the first imaging element, second imaging element and related mutual calibration information of the imaging devices.

Optionally, the arrangement may be configured to model and/or indicate the orientation of potential surface elements including said actual mirroring surface element via indication of surface normal of said elements.

In a further, either supplementary or alternative, embodiment at least one imaging device includes a camera preferably including a light-sensitive radiation sensor surface or sensor matrix. CMOS (complementary metal oxide semiconductor) or CCD (charge-coupled device) technology-based solutions may be utilized, for example. The measurement wavelengths may be determined use scenario-specifically and the applicable light sources/imaging gear be selected correspondingly.

Yet in a further, either supplementary or alternative, embodiment at least one light source has been physically connected to, optionally integrated with, the illumination structure. Optionally, the at least one light source may have been at least partially embedded in the illumination structure. Suitable molding technology such as injection molding may be utilized for the purpose. The illumination structure may be provided with a number of pre-defined surface forms such as slots for accommodating at least part of said at least one light source.

Still in a further, either supplementary or alternative, embodiment at least one light source includes a LED (light-emitting diode), such as LED chip or LED package. Alternatively or additionally, at least one light source may include a projector device such as a so-called data projector device or a slide projection device.

In a further, either supplementary or alternative, embodiment the illumination structure either alone or with the carrier surface for the target object substantially defines at least one shape selected from the group consisting of: spherical shape, dome shape, hemispherical shape, conical shape, truncated cone shape, and cylindrical shape.

In a further, either supplementary or alternative, embodiment at least one light source is controlled via driving voltage or current control, pulse width control and/or pulse density modulation control.

In a further, either supplementary or alternative, embodiment the material of the illumination structure comprises plastic and/or glass.

In a further, either supplementary or alternative, embodiment the arrangement is configured to determine at least one surface-related property of the target object selected from the group consisting of: abruption in the measured surface property such as in the surface orientation or surface normal orientation, surface orientation, surface shape, surface dimensions, and dimensions, size or volume of the target object or a portion thereof. Such property like abruption may be indicative of a surface defect, for example.

In a further, either supplementary or alternative, embodiment the arrangement is configured to apply at least one illumination pattern (image) including a linear intensity ramp or a sinusoidal pattern such as a sinusoidal fringe pattern with sinusoidally changing intensity. The pattern formed on the illumination structure is preferably periodic and contains multiple periods, the overall number thereof optionally falling within a range from about ten to about hundred periods.

In a further, either supplementary or alternative, embodiment the arrangement is configured to apply a sequence of at least four, preferably at least six illumination patterns to obtain at least a respective number of images for determining the desired surface properties.

In a further, either supplementary or alternative, embodiment at least one imaging device is integrated with the illumination structure such as optionally removably attached thereto. Integration may facilitate the required calibration actions to be taken prior to the actual measurements, for instance.

In another aspect, a method for optically measuring a surface of a target object, comprising obtaining a diffusive, semi-transparent illumination structure defining a hollow, preferably curved, surface shape configured to surround the target object at least partially, preferably substantially at least hemispherically, the surface being further provided with at least two, preferably substantially pinhole-like and optionally lens-provided, apertures, wherein a number of light sources are optically coupled to the illumination structure for illuminating the target object via the surface of the illumination structure, obtaining at least two imaging devices, each configured to image the target object via an aperture of said at least two apertures, controlling the number of light sources to form an image sequence of predetermined illumination patterns on the surface of the illumination structure to illuminate the target object with said patterns projected via the surface and instructing the at least two imaging devices to obtain an image of the target object relative to each illumination pattern, and deriving, through the utilization of said patterns utilized and images obtained, a predetermined surface-related property such as shape and/or dimensions of the target object or at least part thereof.

The previously presented considerations concerning the various embodiments of the arrangement may be flexibly applied to the embodiments of the method mutatis mutandis as being appreciated by a skilled person.

The utility of the present invention arises from a plurality of different issues depending on the embodiment. The devised solution enables measuring the 3d shape, orientation and dimensions of various glossy items and related surfaces such as faucet, china, tableware, glass, mirrors, and various other e.g. chromeplated, lacquered or painted surfaces. Even small abruptions/defects may be detected.

The provided technical arrangement further enables formation of various illumination patterns to be used for different measurement methods for both glossy (specular) and scattering (diffusive) surfaces of different target objects. Through the exploitation of photometric imaging even matte, i.e. highly scattering, surfaces may be analyzed and e.g. surface defects detected in connection with the present invention. The achieved accuracy of the measurements is good and the results are generally very reliable.

The provided arrangement is affordable to manufacture and tested, easily obtainable hardware may be utilized therewith. The associated procedure for hardware control and image analysis is both rapid and requires no special hardware either. Ordinary computing elements such as microcontrollers, microprocessors and/or DSPs (digital signal processor) may be applied together with suitable external memory chip(s) or integrated memory. For example, a contemporary laptop or desktop computer may be configured to control the arrangement and/or analyze the obtained images.

The expression "a number of" refers herein to any positive integer starting from one (1), e.g. to one, two, or three.

The expression "a plurality of" refers herein to any positive integer starting from two (2), e.g. to two, three, or four.

The term "surface element" may herein refer to a surface point or area of the target object to be inspected by the suggested optical measurement arrangement. The surface element may thus represent a basic unit from which the target object is considered to be at least logically formed in terms of the measurement. In many measurements, both location and orientation of such surface element is in the interest of the measurer. The dimensions, or size, of the surface elements may vary depending on the resolution of the measurement arrangement as a whole including the resolution of the applied imaging devices, spacing and nature of the light source, configuration of the illumination structure, etc.

The term "substantially pinhole-like aperture" refers herein to an aperture preferably on the order of a pinhole or slightly larger. The aperture may be of magnitude about few hundred micrometers or less, for example. The aperture may be optionally supplemented with an optical element such as a lens, i.e. a lens with a small aperture may be utilized to implement at least one substantially pin-hole aperture of the present invention. For example, the lens may be applied to compensate the otherwise insufficient light exposure provided by the aperture to the sensor of the imaging device. A lens-provided aperture is preferably of magnitude about few millimeters or less (in diameter).

The terms "a" and "an", as used herein, are defined as one or more than one.

Various different embodiments of the present invention are also disclosed in the dependent claims.

BRIEF DESCRIPTION OF THE RELATED DRAWINGS

Next the invention is described in more detail with reference to the appended drawings in which.

DETAILED DESCRIPTION OF THE EMBODIMENTS

Figure 1:
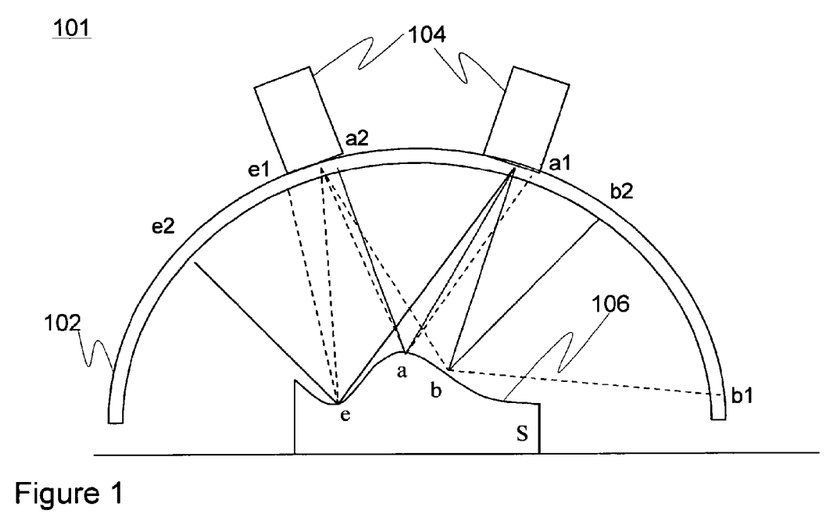
FIG. 1 illustrates the basic principles of an embodiment of the arrangement in accordance with the present invention.

In FIG. 1, an embodiment of an illumination structure, essentially a dome structure, 102 is shown for projecting light provided by a number of embedded or at least optically coupled light sources towards a basically free-form target object, or 'sample', 106 disposed on a predetermined carrier surface, such as a ordinary table or sheet, and surrounded by the illumination structure 102 approximately hemispherically, i.e. above the level of the carrier surface. In some other embodiments, the object 106 could be hung e.g. from a string or be supported by a specific support structure such as a mount, depending on the nature of the illumination structure.

The object 106 may have been substantially centered relative to the illumination structure 102. The illumination structure 102 may generally bear a symmetrical shape as shown in the figure. Two light-sensitive sensor devices, or 'imaging devices', 104 such as digital cameras in many embodiments have been positioned relative to the illumination structure 102 so as to capture light rays emitted by the light sources and reflected by the sample 106 back towards the structure 102. Advantageously the imaging devices 104 have been aligned to image the same sample area (or sample space) from different angles. For example, small openings called as apertures may have been provided to the structure 102 to enable light transmission through it towards the imaging devices 104.

The imaging devices 104 may each contain a substantially planar light-sensitive matrix of multiple imaging elements often called as 'pixels'. The matrix may contain e.g. 1000×1000 pixels or more.

In some other embodiments, a single housing, or a single host apparatus, could contain multiple imaging devices 104 from the standpoint of the present invention, such as multiple camera sensors.

Various light rays emitted by the structure 102 and reflecting, from the surface of the sample 106, back towards the structure 102 and especially towards the associated imaging devices 104 have been depicted as solid and dotted lines in the figure for illustrative purposes.

Basically all or at least most points such as points e, a, b explicitly identified in the top surface of the sample 106 that substantially faces the illumination structure 102, may be measured by the arrangement through recognition and analysis of rays propagated between the illumination structure and light-sensitive sensor surfaces of the imaging devices 102, the propagation incorporating reflection phenomenon at the sample 106 surface.

The reflectivity provided by the surface of the sample 106, to be applicable for shape detection, is preferably specular or comprises at least sufficient specular component. It may also contain diffusive component. Even strongly scattering surfaces (matte surfaces) may be analyzed in a limited sense by the arrangement as presented hereinafter.

Figure 2:
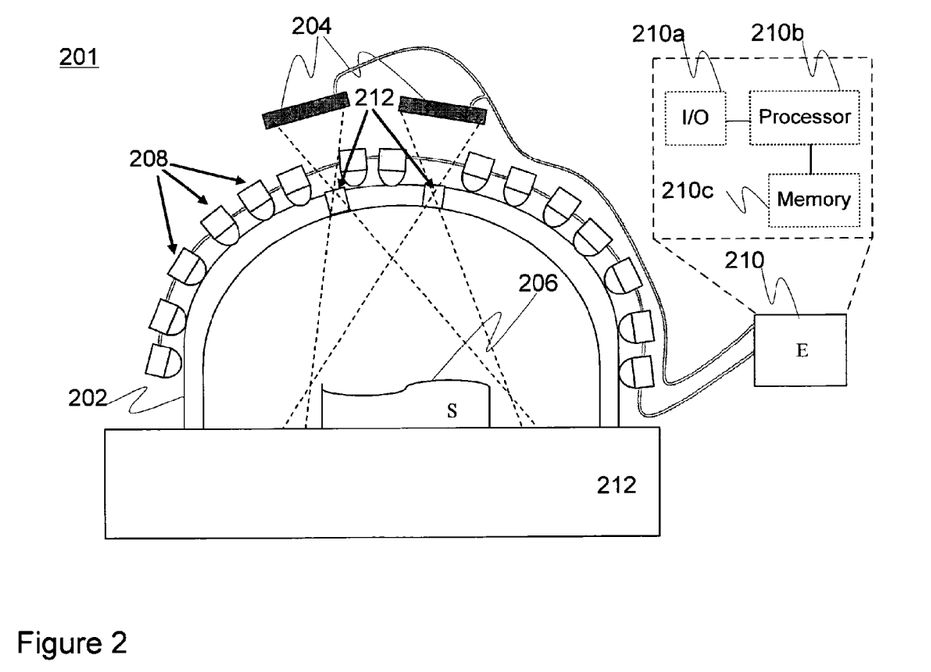
FIG. 2 illustrates various elements of an embodiment of the arrangement in accordance with the present invention.

FIG. 2 represents a more detailed view of an embodiment of the suggested arrangement for conducting optical measurements such as shape and/or dimension measurements.

The potentially high-curvature sample 206 is arranged on a carrier surface 212 that may be provided by a smooth, even plate (e.g. table top surface), for instance. The illumination structure 202 comprises a substantially dome-shaped form practically enclosing the sample 206 between it and the carrier surface 212. The form preferably contains or consists of semi-transparent, diffusive (translucent) material. A plurality of light sources such as LEDs 208, optionally at least functionally organized as a LED matrix, has been arranged to optically couple to the illumination structure 202 such that desired illumination patterns may be established and conveyed by the structure 202 towards the sample 206 for subsequent imaging.

Optionally, the light sources such as LED chips or LED packages have been embedded in the material of the illumination structure 202. E.g. suitable molding technique(s) and/or pre-carved slots accommodating at least part of the light sources 208 may have been utilized for the purpose. Alternatively or additionally, a data projector or e.g. a slide projection system could be utilized as light sources. The light sources 208 could also be external and/or non-contact elements to the illumination structure 202.

Two imaging devices 204 such as CMOS or CCD cameras have been provided external to the illumination structure 202 so as to image the sample by sensing light reflected from the sample 206 via respective pinholes 212. Each imaging device 204 has been preferably configured to image the sample via a dedicated pinhole-type opening. In some other embodiments, different number of imaging devices 204 could be utilized, e.g. three devices, depending on various factors such as the desired coverage of the associated fields of view, configuration and dimensions of the illumination structure, and geometry of the target objects.

'E' 210 refers to the control electronics such as a processing device 210b, memory 210c, and I/O elements 210a (e.g. a data transfer or communication interface, data visualization element such as a display, printer or plotter, a data input element such as a keyboard, a mouse etc.) for controlling, such as synchronizing, the measurement procedures involving the light sources 208 and imaging devices 204. Illumination pattern changes involving light source control may be synchronized relative to the imaging actions of the imaging devices 204 to increase measurement speed, for example.

The control entity 210 may form or be formed from a more general computer device that is suitable for other uses as well. The processing device 210b may include a microprocessor, microcontroller, a DSP, programmable logic array, or a desired plurality of any of those, for instance. The memory 210c may comprise at least one dedicated memory chip or memory integrated with the processor 210b, for instance. The memory 210c may be configured to accommodate a computer program comprising code elements in the form of computer-executable instructions and related other data for controlling the arrangement. Further, the memory 210c may be utilized to host the measurement data and associated analysis results. The computer program may be embodied on a carrier medium such as a memory card or an optical disc.

Regarding the size and spacing of the LEDs 208 or other light sources, the smaller the LEDs etc. are and more closely they are located more accurate illumination patterns can, in principle, be produced and projected on the sample 206. Theoretical minimum distance between light sources is zero. In that case no additional diffusing illumination structures are needed and the light source matrix may itself act as e.g. a dome-shaped display or 'illumination structure' for lighting the sample. However, such zero magnitude spacing may in practical circumstances be sometimes unfeasible since the number of the required light sources increases drastically as well as the required wiring, complexity and the resulting overall price of the arrangement.

However, when the spacing between the light sources is increased, single light sources may become visible in the illumination pattern and images taken due to their spot illumination nature. This can be generally resolved using more effectively diffusing illumination structure material between the light sources and the sample to smooth the illumination. Applicable distance between e.g. LED-type light sources may in many embodiments fall within a range from about 2 to about 10 mm, for example. Together with the increased spacing the diffusing power of the illumination structure such as the dome may need to be increased. The shape of the illumination structure may naturally vary depending on the objects to be imaged and other factors of the desired solution. In addition to a dome or specifically e.g. half-spherical form, full sphere, cylindrical, conical or basically almost any free form shape may, in theory, be utilized.

The size of the illumination structure is scalable in view of different sample sizes and e.g. light sources. In order to get the whole sample measured at one time, it shall be positioned to remain within the viewing area of all the imaging devices 204, i.e. within the camera views, and inside the surrounding shape defined by the illumination structure 202. The material of the illumination structure 202 may include plastic, glass, etc., preferably semi-transparent material.

Control of the intensity of light emitted by the light sources 208 may be realized utilizing e.g. current control or more accurate pulse width or pulse density modulation, for instance. Light source such as LED-specific control may be flexibly achieved through e.g. row and column-based scan of the light source matrix.

Figure 3:
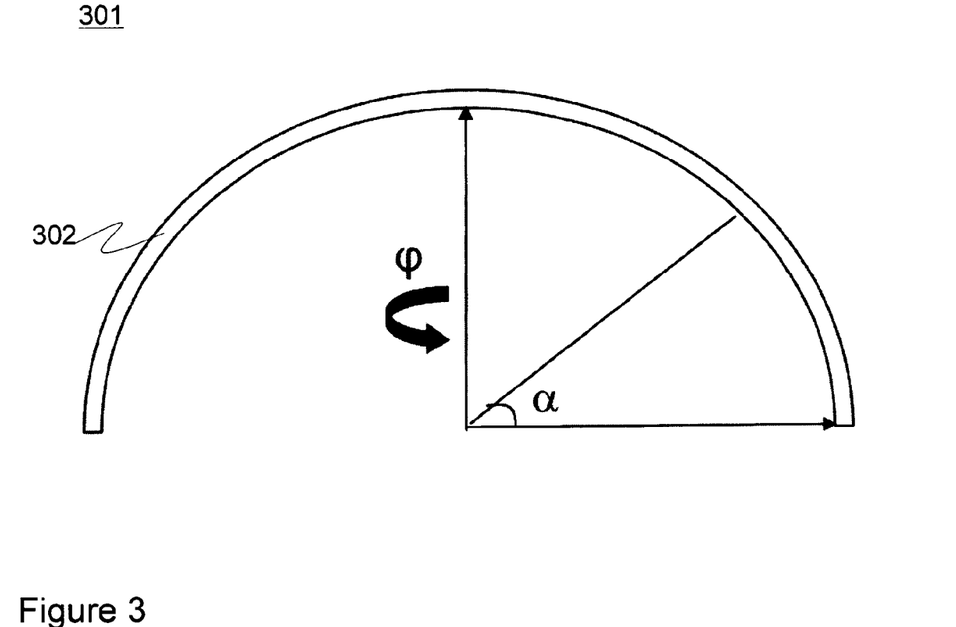
FIG. 3 depicts one example of feasible angle definitions and calculations in connection with various embodiments of the present invention.

With reference to FIG. 3, principles of 3d calculation utilizing the image data are next briefly reviewed. The figure particularly illustrates the angle definitions $\alpha$ and $\phi$ utilized in the disclosed calculation method.

X axis refers to the horizontal axis and Y axis refers to the vertical axis in the shown scenario with a dome-like illumination structure 302. Table 1 below describes the potential illumination patterns utilized. The point, or location, on the dome that reflects from the object surface (surface element) to a camera pixel may be calculated taking e.g. six images using different illumination patterns. Patterns 1 and 2 may be utilized to define the height angle $\alpha$ whereas patterns 3 to 6 may be utilized to define the rotational angle $\phi$.

TABLE 1

Illumination patterns

| Pattern | Definition |
|---|---|
| 1 | LED matrix intensity is linearly related to height angle $\alpha$ so that when $\alpha = 0$ intensity is 0% and when $\alpha = 90$ degrees the intensity is 100%. Intensity pattern is rotationally symmetric around axis Y. |
| 2 | LED matrix intensity is linearly related to height angle $\alpha$ so that when $\alpha = 0$ intensity is 100% and when $\alpha = 90$ degrees the intensity is 0%. Intensity pattern is rotationally symmetric around axis Y. |
| 3 | LED matrix intensity is linearly related to rotational angle $\phi$ so that when $\phi = 0$ intensity is 0% and when $\phi = 180$ degrees the intensity is 100%. Other half of the dome (angles $\phi$ 180 to 360 degrees) is unlit. |
| 4 | LED matrix intensity is linearly related to rotational angle $\phi$ so that when $\phi = 0$ intensity is 100% and when $\phi = 180$ degrees the intensity is 0%. Other half of the dome (angles $\phi$ 180 to 360 degrees) is unlit. |
| 5 | LED matrix intensity is linearly related to rotational angle $\phi$ so that when $\phi = 180$ intensity is 0% and when $\phi = 360$ degrees the intensity is 100%. Other half of the dome (angles $\phi$ 0 to 180 degrees) is unlit. |
| 6 | LED matrix intensity is linearly related to rotational angle $\phi$ so that when $\phi = 180$ intensity is 100% and when $\phi = 360$ degrees the intensity is 0%. Other half of the dome (angles $\phi$ 0 to 180 degrees) is unlit. |

Height angle $\alpha$ may be defined for each image pixel using equation $$\alpha = (\text{Image1} - \text{Image2})/(\text{Image1} + \text{Image2}) \quad (1)$$

Rotational angle $\phi$ between 0 to 180 degrees may be defined for each image pixel using equation $$\phi = (\text{Image3} - \text{Image4})/(\text{Image3} + \text{Image4}) \quad (2)$$

Rotational angle $\phi$ between 180 to 360 degrees may be defined for each image pixel using equation $$\phi = (\text{Image5} - \text{Image6})/(\text{Image5} + \text{Image6}) \quad (3)$$

Different number of images may be alternatively used. Rotational angle $\phi$ may be calculated using two images or potentially more accurate result can be achieved by subsectioning the dome e.g. in 90 degree intervals such a way that first 0 to 90 degree section is measured followed by 90 to 180 degrees section and so on.

Also sinusoidal fringe illumination patterns could be used to calculate reflection point in high accuracy. As with the previous example, the height angle α could be first calculated and then the rotational angle φ.

For determining height angles α an illumination, or a 'lighting', pattern that consist of sinusoidal fringe pattern with several periods may indeed be formed on the dome. The number of sine periods formed on the dome depends on dome size, illuminated sector, LED or more generally light source spacing, and the desired accuracy but may fall within a range from about 10 to about 100 periods, for instance. Sinusoidal pattern on the dome is imaged via the tested, reflective surface of the target object. Three or more images with different phase shifts of the sine pattern are typically needed to calculate the phase of the reflected points. Well-known phase shifting calculation method may be utilized for the calculation. Phase is partially linearly related to the position on the dome. Since the result of phase shifting calculation method is limited between $-\pi$ and $\pi$, the outcome associated with linearly changing intensity pattern is required to define the associated period.

For example, if there are 20 sine periods on the dome surface when the height angle α varies from 0 to 90 degrees, then the phase changes 20 times from $-\pi$ to $\pi$ and each period responds to a 4.5 degree sector. Angle result from linearly changing intensity images can be used to determine which 4.5 degree sector the sine pattern result belongs.

Rotational angle φ may be calculated substantially in a similar fashion.

Different number of sine fringe patterns/images may be utilized depending on the embodiment; phase shifting calculation could be used in connection with three or more patterns/images and Fourier transformation based calculation could be used in connection with one fringe pattern/image.

In some embodiments, the angle calculation results may be utilized for defect detection. When e.g. a glossy surface has a defect it may exhibit a noticeable change in the monitored surface angle. This can be detected from the angle maps. For example, changes surpassing a predetermined threshold for a valid angle variance between adjacent or near-by surface elements may be tracked.

By utilizing the above and/or other alternative illumination patterns, correspondence between the imaging elements, such as pixels, of different imaging devices and surface locations, or 'points', in the inner surface of the illumination structure may be allocated. A pixel of an imaging device and a matching location of the illumination structure, i.e. corresponding transmission point of light, define, for a surface element of the target object, multiple theoretical angle (orientation)/height (distance) combinations from which the correct one may be deduced utilizing the information provided by at least one other imaging device, which is described in further detail hereinbelow. As a result, both the location and orientation of surface elements constituting the overall measured surface may be determined.

Figure 4A:
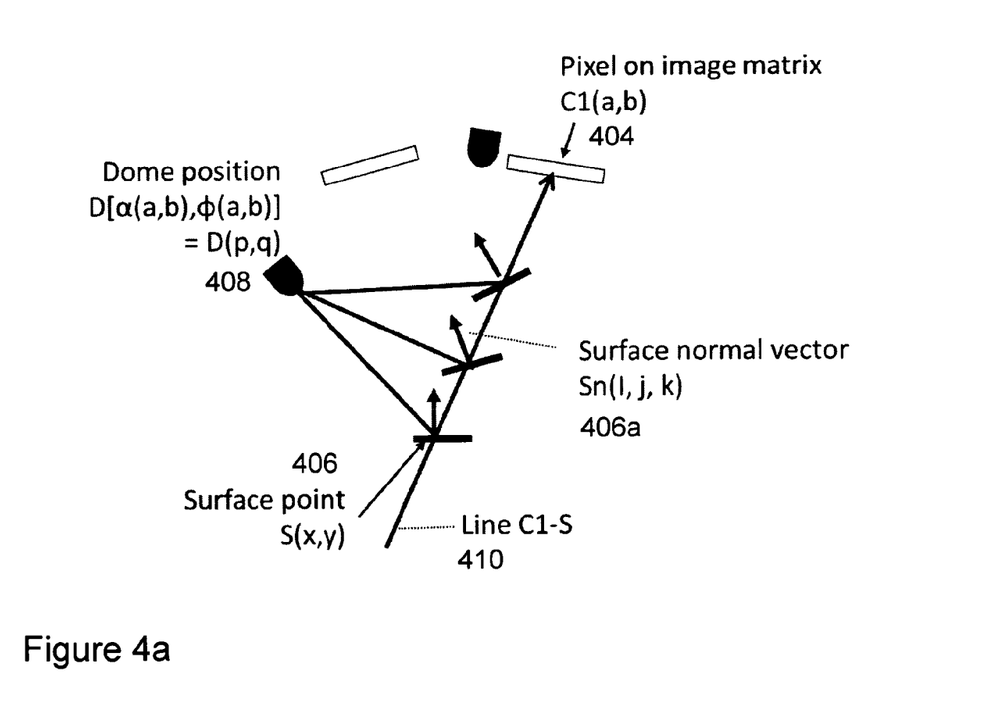
FIG. 4a illustrates the procedures of an embodiment of surface measurement in accordance with the present invention.
Figure 4B:
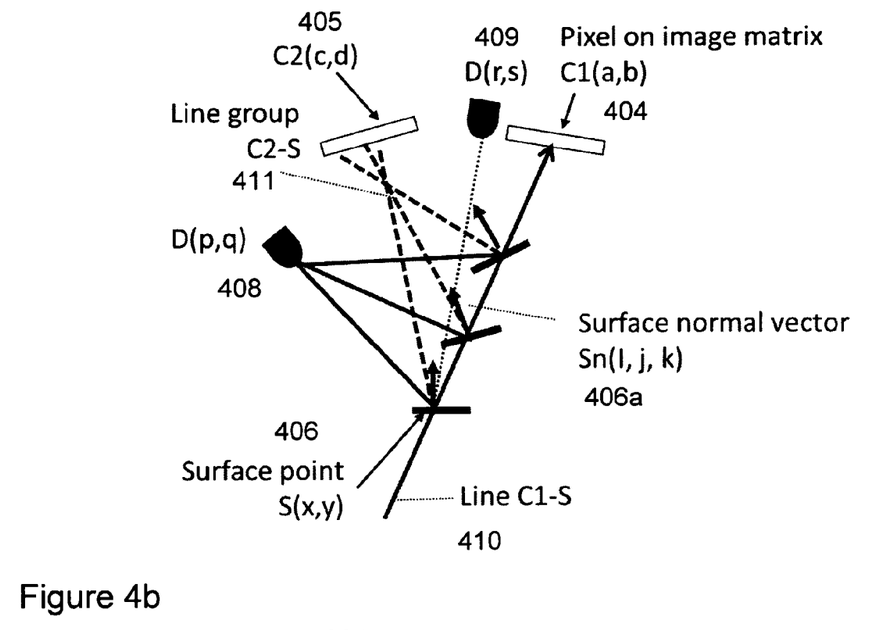
FIG. 4b illustrates further aspects of the aforesaid embodiment of surface measurement.

FIGS. 4a and 4b illustrate the logic behind the procedures of an embodiment of surface measurement in accordance with the present invention in more detail. The figures also contain few explanatory textual remarks facilitating the understanding of the underlying geometric principles exploited.

Figure 5:
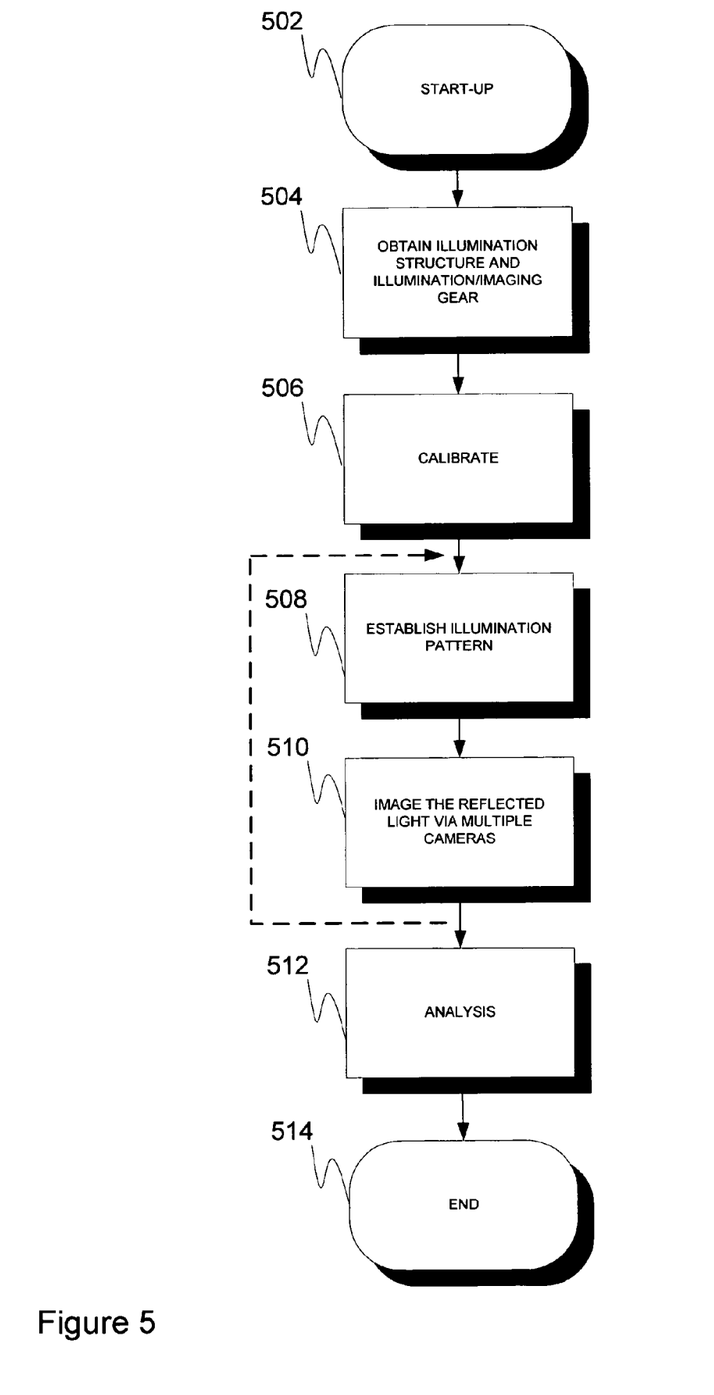
FIG. 5 is a flow diagram of an embodiment of a method for measuring the surface of a target object according to the present invention.

FIG. 5 is a flow diagram of an embodiment of a corresponding method for carrying out the measurements and associated tasks. At 502, the measurement set-up is initially determined based on the surface properties to be measured from the target object(s) and the nature of the target object(s) (glossy, matte, shapes, dimensions, etc.) themselves. Accordingly, at 504 the necessary gear such as illumination structure, e.g. a hemispherical dome or a fully spherical structure, related light sources such as LEDs, imaging devices such as at least two digital camera devices, and control/analysis equipment such as a computer with suitable I/O electronics, are obtained through acquisition of third party components and/or based on in-house manufacturing, for example.

Generally, the 3d shape of a target surface of a target object can be numerically measured utilizing two or more imaging devices such as cameras. First, the relative geometry, orientation and corresponding pixels of the cameras need to be calibrated, however. This may be done at method item 506 exploiting e.g. common stereo camera calibration methods by imaging e.g. a chessboard or other pattern with known dimensions in different positions and calculating the camera parameters and intersection lines for each pixel pair of the cameras. These intersection lines define the distance for each pixel pair combination.

At 508 and 510, a plurality of illumination patterns, i.e. a sequence, is formed by the light sources and the illumination structure, and the corresponding reflection patterns are captured by the cameras, respectively. The light sources and cameras (or other imaging devices) shall be preferably synchronized such that all the desired cameras get at least one image regarding each predetermined illumination pattern. The number and nature of illumination patterns depends on the utilized illumination structure and light sources, cameras, object to be measured and type of measurement done as described herein. The repetitive nature of items 508, 510 (i.e. illumination of a pattern, imaging the pattern, switching into a next pattern, etc.) is illustrated in the figured by a dotted loop-back arrow.

Regarding in particular the analysis item 512 of the method and the associated logic with reference to FIGS. 4a and 4b, the imaging devices such as cameras are treated here, for simplicity, as ideal point aperture cameras.

Angle information $p=\alpha(a,b)$ and $q=\phi(a,b)$ for camera C1 pixel C1(a,b) 404 corresponds to the point D(p,q) 408 on the dome surface that reflects via a surface point S(x,y), or planar 'surface element', 406 (x,y refer to the coordinates on a plane defined by or being at least parallel to a planar carrier surface such as a table surface for the target object) to C1(a,b) 404.

Point C1(a,b) 404 (and the associated aperture of the illumination structure) define a line C1-S 410 where S(x,y) 406 must lie. Line C1-S 410 and point D(p,q) 408 thus create different potential distance-orientation pairs the for surface element S(x,y) 406 that reflects the light emitted by D(p,q) 408 to C1(a,b) 404 in mirror angle. Each potential distance-orientation pair has a different surface normal vector Sn(j,k,l) 406a, i.e. a characterizing orientation of the reflective surface.

Each distance-orientation pair (or 'point' in line C1-S 410) logically corresponds also to one pixel in camera C2 through the associated aperture as C2(c,d) 405, and such pairs establish a line group C2-S 411 (FIG. 4b).

For each of these pixels on the sensor matrix of C2, the mirror reflection (source) point on dome D(r,s) 409 and angle information $r=\alpha(c,d)$ and $s=\phi(c,d)$ have been provided by the measurements. The measured reflection point gives the corresponding surface orientation at intersection of lines C2-S 411 and C1-S 410. The correct pixel C2(c,d) 405, i.e. the pixel whereto the light transmitted by the dome location 409 really reflects from the surface element of the target object measured, is the one that provides, on the basis of the measurements, the same surface orientation at the intersection of lines C2-S 411 and C1-S 410 than the one calculated based on C1(a,b) 404. That is, the actual physical surface element S(x,y) 406 has the same calculated surface normal vector Sn(j,k,l), i.e. surface orientation, regarding both the two analyzed light paths D(p,q)-S(x,y)-C1(a,b) and D(r,s)-S(x,y)-C2 (c,d).

When C1(a,b) 404 and C2(c,d) 405 are solved, the distance and thus the location of the related surface element of the target object, may be uniquely determined also applying the available calibration information.

In the afore-explained manner both the location and orientation of each surface element of the target object may be ultimately determined and the overall surface consisting of the surface elements be modeled and analyzed as the similar procedure may be executed for all the camera pixels.

A skilled person will further realize that since the material of the illumination structure is preferably diffusing in some degree, it is possible to utilize photometric stereo measurement. In connection with a dome-like illumination structure, first half of the dome may be first lit applying uniform intensity followed by imaging the tested surface. Then the other half of the dome may be lit and the tested surface be imaged again. The difference of these two images advantageously indicates potential defects and topological (height) structure of the tested object and related surface. Also more than two lighting directions can be used. Photometric stereo method can be especially used for highly scattering, or 'matte', surfaces of target objects.

The method execution is ended at item 514. The analysis may be continued further or the measurement results obtained so far be stored, transmitted forward and/or provided for review on a display device or printed on paper, for example.

Figure 6:
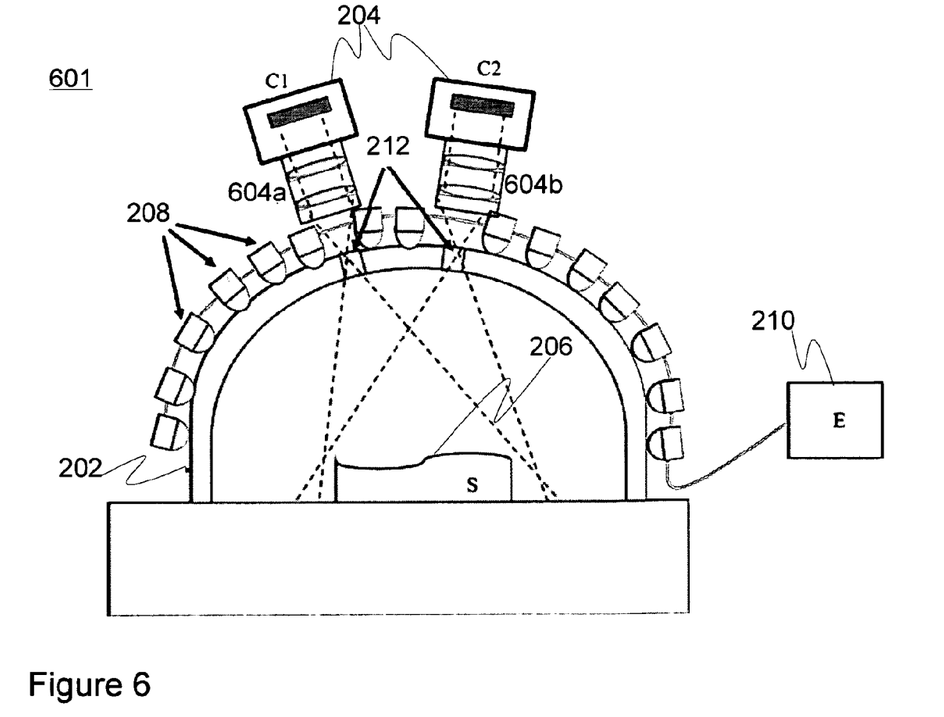
FIG. 6 illustrates an embodiment of the arrangement generally similar to the embodiment of FIG. 2 in more detail.

FIG. 6 illustrates, at 601, an embodiment generally similar to the embodiment of FIG. 2 in more detail. Also here the illumination patterns, i.e. images, are sequentially formed (video sequence) on the illumination structure such as spherical surface 202 and projected therefrom towards the surface of a target object 206. The illumination structure such as spherical surface 202 is thereby utilized as a display element for lighting the sample with image patterns instead of e.g. temporally maximally constant and spatially uniform diffuse illumination. The corresponding (however, distorted) images from the object surface are then captured by the imaging devices 204 preferably in sync with the forming of illumination patterns. By the analysis of the captured images including e.g. analysis of distortions induced thereto (in contrast to the original patterns projected towards the target object's surface) the surface properties such as defects may be detected.

The imaging devices 204 are optically coupled to the target object 206 via corresponding apertures 212, preferably pinhole apertures, provided with lens arrangements 604a, 604. Each lens arrangement 604a, 604b may include a number of lenses, e.g. two or three lenses, which are configured to enable imaging using pinhole-like aperture 212 of the illumination structure 202 in front of the lenses. The magnitude of aperture dimensions may follow the figures given hereinbefore, such as few millimeters, e.g. 1-2 mm, in diameter or even less. Using a small-sized aperture generally reduces the dead zones (shadow regions) in imaging.

Figure 7:
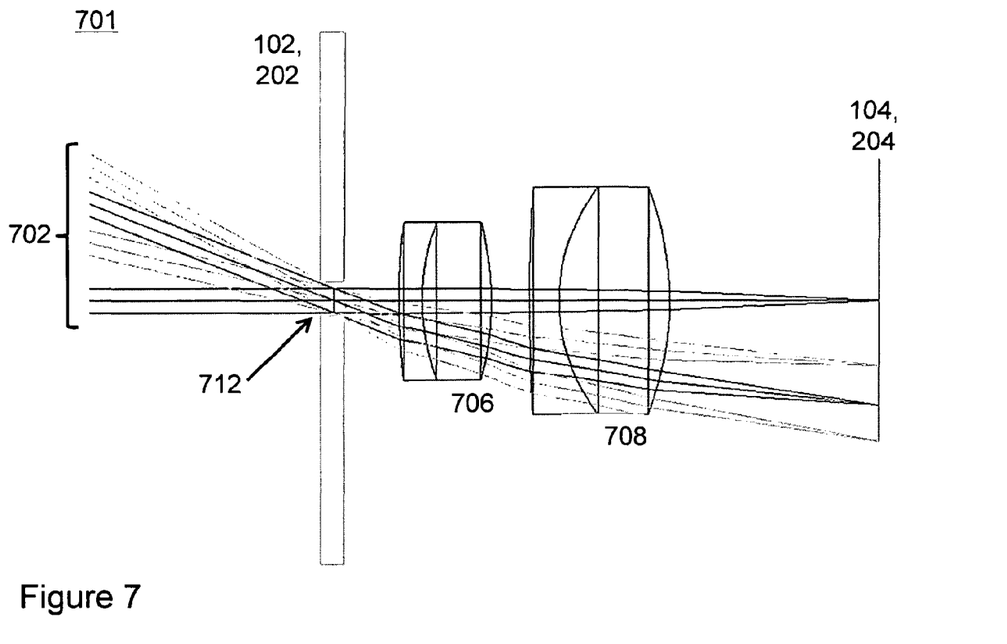
FIG. 7 illustrates an embodiment of applicable pinhole optics for imaging.

FIG. 7 illustrates an embodiment 701 of applicable pinhole optics for imaging. Such solution could be utilized e.g. in connection with the afore-explained embodiments of the present invention. The illumination structure 102, 202 comprises an aperture 712 through which imaging takes place. Light rays 702 from the target object reach a number of lenses 706, 708, such as singlet or doublet lenses, preferably aligned in series, further preferably so as to have a common optical axis.

The lens 706 that is first in the optical path between the target object and imaging device may have a smaller diameter, e.g. few millimeters such as about 3 mm, whereas the second lens has a larger diameter. Accordingly, the mechanical structure around the first lens 706 may be small(er). The diameter of the illumination structure 102, 202 depends on the embodiment and the properties of the target objects (dimensions, etc.) but may be e.g. about 45 centimeters. One example of applicable focal length may then be few millimeters, e.g. about 4-7 millimeters, depending on e.g. the preferred size of the area to be imaged.

Figure 8:
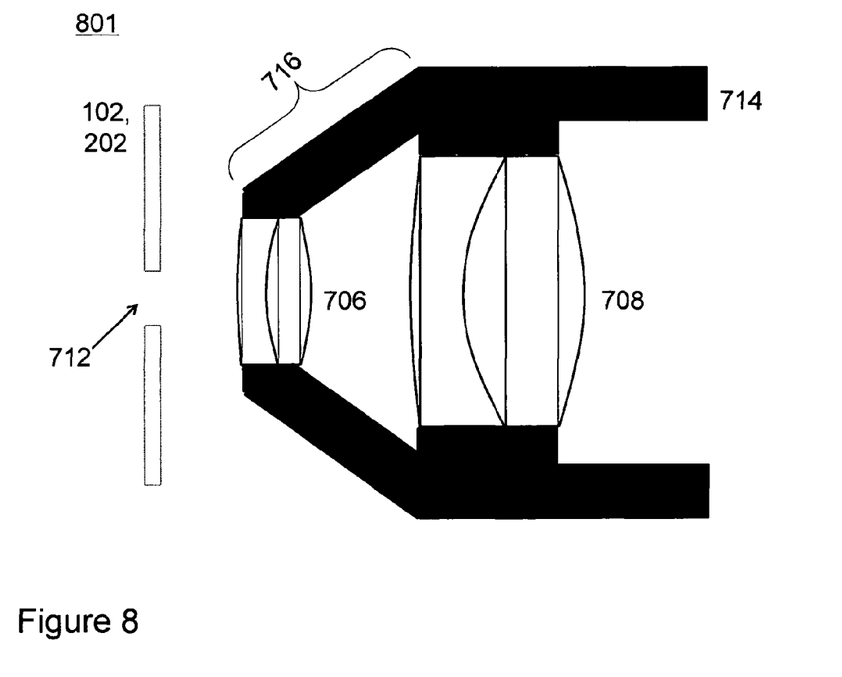
FIG. 8 further illustrates one embodiment of applicable lens configuration in connection with pinhole optics.

FIG. 8 represents, at 801, a further cross-sectional illustration of applicable lens configuration (enlarged in the figure relative to the aperture 712 for clarity reasons) in connection with pinhole optics and e.g. the aforementioned embodiments of the arrangement and method in accordance with the present invention.

The figure illustrates a beveled outer surface portion 716 of the lens arrangement body 714, or "housing structure", accommodating the lens(es). Preferably the beveled edge defines predetermined angle such as about 45 degree angle with the side face of the body or optical axis of the lenses 706, 708 as shown in the figure, but also other configurations are possible depending on the embodiment. Beveling causes less shadowing to the image pattern projection towards the target (and to the resulting imaging) as the blocking effect of the lens arrangement is thereby minimized.

A skilled person may on the basis of this disclosure and general knowledge apply the provided teachings in order to implement the scope of the present invention as defined by the appended claims in each particular use case with necessary modifications, deletions, and additions, if any.

For instance, in some embodiments, only some parts or portions of the target object may need to be analyzed, either in overall or at a time, for which purpose the illumination structure, related light sources, apertures and imaging devices may be configured so as to cover the relevant parts only in terms of the measurement or measurement round. The remaining parts/portions of the target object may be then measured during subsequent measurements by first rotating the object and/or arrangement relative to each other to expose new parts/portions to the illumination and imaging elements.

In some use scenarios, substantially the whole outer surface of a potentially high-curvature 3d object should be measured in one go, which may necessitate utilizing a fully surrounding measurement arrangement such as a sphere-shaped illumination structure and associated all angles-capturing imaging set-up.

Yet in some embodiments, the illumination structure utilized could be formed from several parts that are still configured to functionally form the overall illumination structure while remaining physically separate during the measurements.

Further, in some embodiments the preferred pinhole-like aperture(s) could be replaced with a larger aperture in order to arrange the sensor(s) of the imaging device(s) with sufficient light exposure as alluded hereinbefore. If a lens-based aperture is utilized, the surface of the illumination structure may have to be drilled or carved first to provide a larger diameter hole therein for accommodating the lens still preferably having a smallish aperture of few millimeters, such as two or three millimeters, or less.

Still, in some embodiments the suggested arrangement and method may be utilized for measuring combination objects/ surfaces, i.e. surfaces having both glossy and matte portions. For instance, defects may be tracked from combination surfaces. Different illumination modes (including patterns) may be exploited for the measurements and each surface element ultimately determined based on the best, according to predetermined criterion, result obtained.

The invention claimed is:

1. An arrangement for optically measuring a surface of an target object, comprising:
    a diffusive, semi-transparent illumination structure defining a hollow surface shape configured to surround the target object at least partially, the surface being further provided with at least two apertures,
    a number of light sources optically coupled to the illumination structure for illuminating the target object via the surface of the illumination structure,
    at least two imaging devices, each configured to image the target object via an aperture of said at least two apertures, and
    a control entity configured to instruct said number of light sources to form an image sequence of predetermined illumination patterns on the surface of the illumination structure to illuminate the target object with said patterns projected via said surface, to instruct the at least two imaging devices to obtain an image of the target object relative to each illumination pattern, and to derive, through the utilization of said patterns utilized and images obtained, a predetermined surface-related property of the target object,
    wherein at least one of said two apertures is associated with a lens arrangement comprising a number of lenses, and
    wherein the lens arrangement further comprises a body portion facing the aperture with a beveled edge to reduce the shadowing effect of the lens arrangement relative to the illumination structure.

2. The arrangement of claim 1, configured to apply the image data of multiple images to determine the position and/or orientation of a surface element of the target object through determination of an imaging element pair, including an imaging element from each of two imaging devices, wherein the surface element is in mirror angle relative to both imaging elements in view of two light-transmitting surface locations of the illumination structure and associated rays reflected from the surface element of the target object.

3. The arrangement of claim 2, configured to determine the orientation of the surface element based on the mirror angle found during the imaging element pair determination.

4. The arrangement of claim 2, configured to determine the position of the surface element of the target object based on said imaging element pair and calibration information regarding the relationship of different imaging elements between the two imaging devices, said information indicating knowledge about potential light ray intersections between the imaging elements of the imaging devices.

5. The arrangement of claim 1, wherein at least one of the two imaging devices includes a CMOS (complementary metal oxide semiconductor) or CCD (charge-coupled device) camera.

6. The arrangement of claim 1, wherein at least one of the number of light sources includes a LED (light-emitting diode) chip, a LED package, or an OLED (organic LED).

7. The arrangement of claim 1, wherein at least one of the number of light sources is integrated with the illumination structure.

8. The arrangement of claim 1, wherein the illumination structure substantially defines at least one shape selected from the group consisting of: spherical shape, dome shape, hemispherical shape, conical shape, truncated cone shape, and cylindrical shape.

9. The arrangement of claim 1, wherein the lens arrangement comprises a plurality of lenses arranged in series and wherein a lens of said plurality of lenses disposed prior to at least one other lens of said plurality of lenses in the optical path has a diameter smaller than the at least one other lens.

10. The arrangement of claim 1, wherein at least one of said number of light sources is controlled via pulse width or pulse density modulation.

11. The arrangement of claim 1, wherein the illumination structure contains or substantially consists of plastic or glass material.

12. The arrangement of claim 1, wherein the arrangement is configured to determine at least one surface-related property of the target object selected from the group consisting of: surface orientation, spatial abruption in the measured surface property, surface shape, surface dimensions, object dimensions, object size, and object volume.

13. The arrangement of claim 1, configured to apply at least one illumination pattern including a linear intensity ramp or a sinusoidal pattern with sinusoidally changing intensity.

14. The arrangement of claim 1, configured to apply a sequence of at least four illumination patterns to obtain at least a respective number of images for determining the desired surface properties.

15. The arrangement of claim 1, configured to apply photometric stereo illumination patterns and imaging for measuring a predetermined surface property of a scattering surface of the target object.

16. The arrangement of claim 1, comprising a projector device as at least one of the number of light sources.

17. An arrangement for optically measuring a surface of a target object, comprising:
    a diffusive, semi-transparent illumination structure defining a hollow surface shape configured to surround the target object at least partially, the surface being further provided with at least two apertures,
    a number of light sources optically coupled to the illumination structure for illuminating the target object via the surface of the illumination structure,
    at least two imaging devices, each configured to image the target object via an aperture of said at least two apertures, and
    a control entity configured to instruct said number of light sources to form an image sequence of predetermined illumination patterns on the surface of the illumination structure to illuminate the target object with said patterns projected via said surface, to instruct the at least two imaging devices to obtain an image of the target object relative to each illumination pattern, and to derive, through the utilization of said patterns utilized and images obtained, a predetermined surface-related property of the target object,
    the arrangement being configured to determine
    for a first imaging element of a first imaging device, a matching first light-transmitting surface location of the illumination structure based on image data of multiple images obtained, said matching first light-transmitting surface location supplying light to the first imaging element via an actual, mirroring surface element of the target object,
    through utilization of said first imaging element and the associated first aperture of said illumination structure, a first line defining a plurality of potential surface elements each of which having a certain orientation and being in mirror angle relative to said first surface location and said first imaging element, said plurality of potential surface elements also containing said actual mirroring surface element, and a second imaging element of a second imaging device, with a matching, second light-transmitting surface location of the illumination structure based on image data of multiple images obtained, wherein the second image element and the associated second aperture of the illumination structure define a second line having an intersection with the first line at one of said plurality of potential surface elements also being in mirror angle relative to said second surface location and said second imaging element, said one of said plurality of potential surface elements being thus indicative of said actual mirroring surface element including the orientation thereof, and the position of said actual mirroring surface element utilizing the first imaging element, second imaging element and related mutual calibration information of the imaging devices in connection with the arrangement.

18. A method for optically measuring a surface of a target object, comprising obtaining a diffusive, semi-transparent illumination structure defining a hollow surface shape configured to surround the target object at least partially, the surface being further provided with at least two apertures, wherein a number of light sources are optically coupled to the illumination structure for illuminating the target object via the surface of the illumination structure, wherein at least one of said two apertures is associated with a lens arrangement comprising a number of lenses, and wherein the lens arrangement further comprises a body portion facing the aperture with a beveled edge to reduce the shadowing effect of the lens arrangement relative to the illumination structure, obtaining at least two imaging devices, each configured to image the target object via an aperture of said at least two apertures, controlling the number of light sources to form an image sequence of predetermined illumination patterns on the surface of the illumination structure to illuminate the target object with said patterns projected via said surface and instructing said at least two imaging devices to obtain an image of the target object relative to each illumination pattern, and deriving, through the utilization of said patterns utilized and images obtained, a predetermined surface-related property of the target object or at least part thereof.

19. A computer program embodied in a non-transient computer-readable medium and comprising code means adapted, when run on a computer apparatus, to execute the items of controlling and deriving according to claim 18.

20. A method for optically measuring a surface of a target object, comprising:

obtaining a diffusive, semi-transparent illumination structure defining a hollow surface shape configured to surround the target object at least partially, the surface being further provided with at least two apertures, wherein a number of light sources are optically coupled to the illumination structure for illuminating the target object via the surface of the illumination structure;

obtaining at least two imaging devices, each configured to image the target object via an aperture of said at least two apertures;

controlling the number of light sources to form an image sequence of predetermined illumination patterns on the surface of the illumination structure to illuminate the target object with said patterns projected via said surface and instructing said at least two imaging devices to obtain an image of the target object relative to each illumination pattern; and deriving, through the utilization of said patterns utilized and images obtained, a predetermined surface-related property of the target object or at least part thereof;

illuminating the target object by the number of light sources optically coupled to the illumination structure for illuminating the target object via the surface of the illumination structure;

imaging the target object by at least two imaging devices, each configured to image the target object via an aperture of said at least two apertures; and instructing in control of a control entity configured to instruct said number of light sources to form an image sequence of predetermined illumination patterns on the surface of the illumination structure to illuminate the target object with said patterns projected via said surface, to instruct the at least two imaging devices to obtain an image of the target object relative to each illumination pattern, and to derive, through the utilization of said patterns utilized and images obtained, a predetermined surface-related property of the target object;

determining, by said arrangement being configured to determine for a first imaging element of a first imaging device, a matching first light-transmitting surface location of the illumination structure based on image data of multiple images obtained, said matching first light-transmitting surface location supplying light to the first imaging element via an actual, mirroring surface element of the target object, through utilization of said first imaging element and the associated first aperture of said illumination structure, a first line defining a plurality of potential surface elements each of which having a certain orientation and being in mirror angle relative to said first surface location and said first imaging element, said plurality of potential surface elements also containing said actual mirroring surface element, and a second imaging element of a second imaging device, with a matching, second light-transmitting surface location of the illumination structure based on image data of multiple images obtained, wherein the second image element and the associated second aperture of the illumination structure define a second line having an intersection with the first line at one of said plurality of potential surface elements also being in mirror angle relative to said second surface location and said second imaging element, said one of said plurality of potential surface elements being thus indicative of said actual mirroring surface element including the orientation thereof, and the position of said actual mirroring surface element utilizing the first imaging element, second imaging element and related mutual calibration information of the imaging devices in connection with the arrangement.

21. A computer program embodied in a non-transient computer-readable medium and comprising code means adapted, when run on a computer apparatus, to execute the items of controlling and deriving according to claim 20.

* * * * *